United States Patent [19]

Mercereau

[11] Patent Number: 5,552,323
[45] Date of Patent: Sep. 3, 1996

[54] METHOD OF BLENDING AN ANTICOAGULANT

[76] Inventor: Steven F. Mercereau, 4911 W. Lake Dr., Conyers, Ga. 30208

[21] Appl. No.: 285,054

[22] Filed: Aug. 3, 1994

[51] Int. Cl.$^6$ .................................................. G01N 33/86
[52] U.S. Cl. ................. 436/18; 436/69; 436/176; 514/56; 536/21; 128/760; 128/763; 128/765; 128/770; 128/771
[58] Field of Search ................. 436/18, 69, 176; 514/56; 536/21; 128/760, 763, 765, 770, 771

[56] References Cited

U.S. PATENT DOCUMENTS

| | | | |
|---|---|---|---|
| 4,045,612 | 9/1993 | Thiel | 424/183 |
| 4,252,118 | 2/1981 | Richard | 128/218 P |
| 4,479,799 | 10/1984 | Thiel | 604/187 |
| 4,687,000 | 9/1987 | Eisenhardt | 128/760 |
| 5,336,620 | 8/1994 | Mancilla et al. | 436/18 |
| 5,399,318 | 3/1995 | Mancilla et al. | 422/100 |

OTHER PUBLICATIONS

Toffaletti, "Use of Novel Preparations of Heparin to Eliminate Interference in Ionized Calcium Measurements: Have All the Problems Been Solved", Clinical Chem. vol. 40, No. 4, 1994 pp. 508–509.

Toffaletti, "Effects of Blended Lithium–Zinc Heparin on Ionized Calcium & General Clinical Chemistry Tests", Clin. Chemistry, vol. 41, No. 2, 1995, pp. 328–329

Lyon et al., Evaluation of Dry Lithium Heparin and Zinc heparin anticoagulants for Whole Blood Ionized Calcium Measurements, Clin. Chem, vol. 39, No. 6, 1993; pp. 1175–1176.

The United States Pharmacopiea/The National Formulary, United States Pharmacopial Convention, Inc. Jan. 1, 1990, pp. 102, 103, 185, 186, 441, 442, 631–634, 1747, 2025.

Martell Arterial Blood Gas Collection System, Martell Medical Products, Inc., Oct. 1993.

Interference In Ionized Calcium Measurements, Landt, Michael, et al., Clinical Chemistry, pp. 565–570, vol. 40, No. 4, 1994.

Evaluation of Syringe Products Supplied by Martell Medical Products, John Toffaletti.

*Primary Examiner*—Jill Warden
*Assistant Examiner*—Sharidan Carrillo
*Attorney, Agent, or Firm*—Kennedy & Kennedy

[57] ABSTRACT

A blended heparin salt for use as an anticoagulant in a blood sample, which substantially eliminates a skew in a determined amount of ionized calcium imparted by the heparin in the blood sample. The blended heparin salt comprises a proportional blend of a zinc salt of heparin and a lithium salt of heparin the salts in a ratio of 1-to-a-fractional-value-less-than-one of the zinc salt of heparin to the lithium salt of heparin by weight based on the USP potency of the salts, the fractional value determined by the ratio of the zinc available per unit of USP potency in the zinc salt of heparin to a predetermined amount of zinc per USP potency to be provided by the blended heparin salt. Methods of blending the proportional amounts of the zinc salt and the lithium salt of heparin are disclosed.

2 Claims, No Drawings

5,552,323

METHOD OF BLENDING AN ANTICOAGULANT

TECHNICAL FIELD

The present invention relates to anticoagulants for use with analysis of blood samples and mettles of blending anticoagulants. More particularly, the present invention relates to heparin salts and to methods of blending heparin salts.

BACKGROUND OF THE INVENTION

Medical evaluations typically rely on a variety of tests for determining physiological conditions of patients. One common test is known as electrolyte analysis. This test determines the percentages of several ionized minerals in samples of blood taken frown patients. These ionized minerals include calcium, sodium, and potassium. Other tests can determine the pH value of the blood as well as other physiological indicators. The blood samples are typically collected in sampling syringes. The samples taken from the patients often consist of about three milliliters of blood. Them are a number of sampling syringes known in the art for drawing and holding samples for testing.

The samples of blood typically are moved to laboratories for testing and analysis shortly after being obtained from the patients. Testing preferably should occur within 30 minutes or less of the samples being drawn. Dissolved gases in the blood begin diffusing from the samples immediately. The blood begins to coagulate and bind the minerals in the fluidal blood together. Coagulation skews the test results because the bound minerals resist detection during the analysis which only detects the free ionized minerals in the fluidal blood. If some of the minerals are clotted out of the fluid, the analysis results in a false determination of mineral content percentages less than is actually present in the blood of the patients being tested. Such incorrect determinations can lead to mis-diagnosis, which may lead to injury to the patients.

To reduce test interference caused by coagulation, sampling syringes typically include anticoagulants. The anticoagulants delay the coagulation of the blood and provide a larger window of time after drawing samples of blood to begin testing. The anticoagulant commonly used in sampling syringes is a compound known as heparin. Heparin is typically supplied in the form of a lyophilized powder or a liquid. The heparin is placed in a sample-holding chamber of a sampling syringe. The liquid blood drawn from the patient into the sampling syringe dissolves or dilutes the heparin. The heparin reduces the coagulation of the blood for a period of time, which period provides time to transfer the sampling syringe to a laboratory for analysis of the sample of blood.

Typically, the heparin is supplied in the form of a salt. Various metal salts of heparin are known, including lithium salt of heparin, calcium salt of heparin, and zinc salt of heparin. These metals are cations which may bind with the heparin at anion binding sites. It is considered that in solution the cations continuously dissociate from and re-associate with the anion binding sites on the heparin molecule, and reach a state of equilibrium with the other cations in the fluidal blood sample. These cations compete for the anion binding site depending on their respective binding affinities and proportionate concentrations while the heparin performs the anticoagulation function.

These metals have varying affinity for binding to the heparin. Zinc binds more strongly with heparin than calcium which binds more strongly than lithium. These differences in binding affinity of the cation and the anion have an impact on the analysis of the blood sample. The particular, studies show that the analysis of blood containing a zinc salt of heparin detects an increased amount of ionized calcium in the blood sample over that detected in a control sample of blood, possibly by detecting the dissociated zinc as ionized calcium. In contrast, studies show that the analysis of blood containing a lithium salt of heparin detects a decreased amount of ionized calcium in the blood sample, possibly due to the ionized calcium occupying the anion binding sites on the heparin molecule which are vacated by the dissociated lithium and the associated calcium is undetected by the analyzer. The particular salt of heparin accordingly effects the perceived amount of ionized calcium in contrast to the actual amount as indicated by a control sample. Also, due to variances in the raw material used to manufacture the heparin molecule, the heparin has varied potencies. Each batch of a salt of heparin is tested and a certificate that accompanies the packaged heparin salt sets forth the determined USP potency. Such differences may lead to incorrect diagnosis of the physiological condition of the patient. Misdiagnosis may lead to incorrect treatment or failure to treat, to the possible injury of the patient.

Accordingly, there exists a need in the art for a heparin anticoagulant which substantially eliminates a skew in a determined amount of ionized calcium imparted by the heparin in the blood samples and an improved method of blending a salt of heparin for use as an anticoagulant.

SUMMARY OF THE INVENTION

The present invention meets the need in the art by providing a blended heparin salt anticoagulant, and methods of making such anticoagulant, that substantially reduces a skew imparted by the heparin in a determined amount of ionized calcium in a blood sample. The blended heparin salt in a preferred embodiment comprises a proportional blend of a zinc salt of heparin and a lithium salt of heparin based on a respective value of heparin potency of the salts. The blended heparin salt contains the zinc and lithium salts blended in a ratio of 1-to-a-fractional-value-less-than-one of the salt with the lower heparin potency to the salt with the higher USP potency by weight. The fractional value is representative of the ratio of the respective values of heparin potency of the salt, by weight. The zinc salt and the lithium salt of heparin are preferably saturated, with the zinc salt of heparin having a concentration of about 12% zinc and the lithium salt of heparin having a concentration of about 3.5 to 4.5% lithium. Using one known measuring system, the USP potency of the zinc salt of heparin and the lithium salt of heparin is preferably between about 150 and 189 units.

A method of blending a zinc salt of heparin and a lithium salt of heparin to form a blended heparin salt anticoagulant comprises supplying the zinc salt of heparin and the lithium salt of heparin each with a respective predetermined activity unit potency (known as USP potency). The method selects for a basis salt the one of the salts having the lower of the respective activity trait potency. The method determines a fractional value less than one of the activity unit potencies of the salt having the lower potency relative to the salt having the higher activity unit potency, for a blending ratio. The basis salt and the other of the salts are blended together in a 1-to-the-fractional-value ratio by weight to form the blended heparin anticoagulant. This blended heparin anticoagulant has a combined activity unit potency. A predetermined number of units available in the blended heparin salt are placed in a blood sampling syringe with blood drawn from a patient for analysis. The heparin salt of the method substantially eliminates the skew imparted by the heparin anticoagulant to the measured value of ionized calcium in the blood sample.

In another aspect of the present invention, a blended heparin salt comprises a proportional blend of a zinc salt of heparin and a lithium salt of heparin. The salts each have a respective value of heparin potency, and the zinc salt has a concentration of zinc per heparin unit that is equal or greater than a predetermined concentration of zinc to be provided by the blended heparin salt. The blended heparin salt includes the zinc salt and the lithium salt in a ratio of 1-to-a-fractional-value of the zinc salt of heparin to the lithium salt of heparin by weight. The fractional value for the amount of the lithium salt to add is determined by a quotient less 1.0, the quotient defined by dividing the zinc per heparin unit available in the zinc salt of heparin by the predetermined amount of zinc per heparin unit to be provided by the blended heparin salt. The lithium salt is preferably saturated. Using one known measuring system, the predetermined amount of zinc ranges from about $2.4 \times 10^{-4}$ milligrams zinc per USP unit of heparin activity to about $4.8 \times 10^{-4}$ milligrams zinc per USP unit of heparin activity, with a preferred predetermined amount of zinc about $3.63 \times 10^{-4}$ milligrams zinc per USP unit of heparin activity.

A method of blending this heparin salt comprises supplying a zinc salt of heparin having a heparin potency and a concentration of zinc per USP unit that equals or exceeds a predetermined mount of zinc per heparin unit to be provided by the blended heparin salt for use as an anticoagulant in a blood sample held in a sampling syringe. A quotient less 1.0 from this comparison results in a fractional portion that multiplied by the heparin potency of the zinc salt of heparin, indicates the amount of additional USP potency units to add blendingly to provide the predetermined amount of zinc per heparin unit in the blended heparin salt. The quotient is defined by dividing the zinc per USP unit available in the zinc salt of heparin by the predetermined amount of zinc per heparin unit to be provided by the blended heparin salt. The additional diluting heparin potency is preferably supplied by a lithium salt of heparin having a predetermined heparin potency. Dividing the additional number of heparin units needed to blend with the zinc salt by the USP potency of the lithium determines the amount of the lithium salt of heparin to blend with the zinc salt of heparin in a ratio of the determined-amount-to-1 by weight respectively to form a blended heparin salt that provides the predetermined amount of zinc per unit of heparin potency. A selected number of units of the blended heparin salt based on USP potency are placed in a sampling syringe with a blood sample to substantially eliminate the skew in the measured amount of ionized calcium in the blood sample imparted by the heparin anticoagulant.

DETAILED DESCRIPTION OF THE DISCLOSED EMBODIMENTS

The present invention provides a blended heparin salt anticoagulant, and methods of making such anticoagulant, that substantially reduces a skew in the detected amount of ionized calcium in a blood sample, which skew is imparted by the heparin. The heparin salt of the present invention comprises a proportional blend of a zinc salt of heparin and a lithium salt of heparin. Each of these salts has a respective value of USP potency, which is one known system for measuring activity. The blended heparin salt contains the zinc and lithium blended in a ratio of 1-to-a-fractional-value-less-than-one of the salt with the lower USP potency to the salt with the higher USP potency by weight. The fractional value is representative of the ratio of the respective values of lower USP potency to the higher USP potency of the lower salts, by weight. The zinc salt and the lithium salt of heparin are preferably saturated, with the zinc salt of heparin about 12% zinc and the lithium salt of heparin about 3.5 to 4.5% lithium. The USP potency of the zinc salt of heparin and the lithium salt of heparin is between about 150 and 189 units.

The manufacturing process For salts of heparin results in the heparin having varied potency. Each salt has a respective predetermined activity unit potency (known as USP potency). The method of blending according to the present invention selects for a basis salt the one of the zinc and the lithium salts having the lower of the respective activity unit potency. The method determines a fractional value less than one of the salt having the lower activity unit potency relative to the salt having the higher activity unit potency, for a blending ratio. The basis salt and the other of the zinc salt and the lithium salt are blended to ether in a 1-to-the-fractional-value ratio by weight to form a blended heparin anticoagulant. This blended heparin anticoagulant has a combined activity unit potency. A predetermined number of units available in the blended heparin salt are placed in a blood sampling syringe with blood drawn from a patient for blood analysis to substantially eliminate the skew imparted by the heparin anticoagulant to the measured value of ionized calcium in the blood sample.

EXAMPLE 1

A heparin salt was prepared by blending a zinc salt of heparin and a lithium salt of heparin obtained from Celcus Laboratories, Inc., Cincinnati, Ohio, according to the method described above. The blended salt was formed on a 1:1 ratio based on potency. The zinc salt had a concentration of 12% zinc and 149 units per milligram USP potency. The lithium salt had a concentration of 3.64% lithium and 178 units per milligram USP potency. Table 1 below reports the difference in detected ionized calcium in comparison with uncoagulated whole blood that did not include an anticoagulant, measured in millimoles per liter.

Five syringes were heparinized with 50 units (USP potency) of zinc lithium heparin salt blended together in a ratio based on potency. Blood samples were obtained and analyzed for ionized calcium content. These results were compared with the ionized calcium content in the uncoagulated whole blood of the sample. The results were considered acceptable if the differences in the means and the standard deviations were within 0.015 millimoles per liter. The results are shown below in Table 1.

TABLE 1

| Detected Ionized Calcium Compared With Uncoagulated Whole Blood | | |
|---|---|---|
| Contents of Syringe | Mean Difference | SD Difference |
| Zn:Li | 0.002 | 0.004 |
| Li heparin | −0.030 | 0.010 |
| Zn heparin | 0.032 | 0.013 |

The blended Zn:Li heparin salt provided a counterbalanced effect on the determination of the ionized calcium contained in the blood samples as compared with the whole blood having no anticoagulant. The lithium heparin salt had a negative skew; the zinc heparin salt had a positive skew.

EXAMPLE 2

The method described above of blending the zinc and lithium heparin salts was repeated for two different lots of the zinc salt and the lithium salt of heparin. Lot 1 used the salts described above in Example 1. Lot 2 used a zinc salt with 165 units per milligram USP potency and a lithium salt with 173 units per milligram USP potency. These salts were saturated at 12% zinc and 3.64 % lithium, respectively. The results are shown below in Table 2.

TABLE 2

| Detected Ionized Calcium Compared With Uncoagulated Whole Blood | | |
|---|---|---|
| Contents of Syringe | Mean Difference | SD Difference |
| Zn:Li (Lot 1) | 0.006 | 0.005 |
| Zn:Li (Lot 2) | 0.006 | 0.009 |
| Li heparin | −0.044 | 0.021 |
| Zn heparin | 0.038 | 0.013 |

The Zn:Li heparin salts in Lots 1 and 2 were blended based on potency using salts of different potencies. These blended heparin salts provided a consistent counterbalanced effect on the determination of the ionized calcium contained in the blood samples as compared with the whole blood having no anticoagulant. The lithium heparin salt had a negative skew; the zinc heparin salt had a positive skew.

The blending of the zinc lithium salt in Lot 2 is described below. The zinc salt having the lower activity unit potency of 165 units per milligram (USP potency) was selected as the basis salt. A fractional value less than one was determined by comparing the potency of the basis salt (165 u/mg) with the activity unit potency of the lithium salt (173 u/mg) to determine a fractional value less than one, or 0.954. This is the fractional amount of the lithium salt to blend with the zinc salt to yield a 1:1 blend based on potency. Thus, one milligram of the zinc salt is blended with 0.954 milligram of the lithium salt. The total USP potency available in the 1.954 milligram blended heparin salt is 330 USP units, as computed by adding the 165 u/mg from the zinc salt and 0.954 times the 173 u/mg from the lithium salt.

The blended heparin salt is used in a sampling syringe to prevent coagulation of the blood drawn for testing. Typically, the anticoagulant is provided at 50 units USP potency for each syringe. The blended heparin salt in the above example provides a total of 330 USP units in the 1.954 milligrams, or 169 units per milligram. A sampling syringe with 50 units would have 0.296 milligrams of the blended heparin salt, as computed by dividing the 50 units by the 169 units per milligram. The blended heparin salt in the sampling syringe substantially eliminates the skew in the measured amount of ionized calcium in the blood sample imparted by the heparin anticoagulant.

In another aspect of the present invention, a salt of heparin can be formed using a zinc salt of heparin having a concentration of zinc less than saturation. The method of forming this salt of heparin determines the amount of zinc available from the zinc salt per unit of USP potency. Thus, the method of blending and the resulting blended heparin salt takes into consideration both the zinc concentration in a zinc salt of heparin for blending and the potency of the zinc salt of heparin in determining a blend ratio for forming the blended heparin salt. The amount of zinc per USP unit of the zinc salt equals or exceeds a predetermined amount of zinc per USP unit to be delivered by the blended heparin salt.

The amount of zinc available from the zinc salt per unit of USP potency is compared with the predetermined amount of zinc per unit of USP potency to be delivered by the blended heparin salt for use as an anticoagulant. The comparison results in a quotient by dividing the predetermined amount of zinc per unit by the available amount of zinc per unit in the zinc salt. The quotient less 1.0 from this comparison provides a percentage by which the USP potency is to be increased in order for the zinc heparin to deliver the predetermined amount of zinc per unit of USP potency. In a preferred embodiment, the increase in USP potency is obtained by blending into the zinc salt of heparin a determined amount of a lithium salt of heparin that provides the additional USP potency.

EXAMPLE 3

As an example, a blended heparin salt of the present invention is made by providing a zinc salt of heparin having a predetermined USP potency of 172 units per milligram and a predetermined concentration of zinc at 7.5%. Dividing the 7.5% concentration by the 172 USP potency yields $4.36 \times 10^{-4}$ milligrams zinc per USP unit. This amount of zinc delivered by the zinc salt is compared with a predetermined amount of zinc to be delivered by the blended heparin salt of the present invention. The predetermined amount zinc to be delivered ranges from about $2.4 \times 10^{-4}$ milligrams per unit of USP potency to about $4.8 \times 10^{-4}$ milligrams per unit of USP potency, as discussed below. In a preferred embodiment, the predetermined amount of zinc to be delivered by the blended salt is $3.63 \times 10^{-4}$ milligrams per unit of USP potency.

The quotient from the comparison of the $4.36 \times 10^{-4}$ mg Zn per unit with the $3.63 \times 10^{-4}$ mg Zn per unit yields 1.20. The fractional portion greater than one (i.e., the additional amount indicates the additional percent of USP potency to blend with the zinc salt of heparin to reduce the amount of zinc relative to the total activity in the blended heparin salt of to provide the predetermined amount of zinc in the blended heparin salt. Multiplying this additional percentage by the USP potency of the zinc salt of heparin yields the additional number of units of USP potency required to be blended with the zinc salt to deliver the predetermined amount of zinc per USP unit of the blended heparin salt. In this example, the additional number of USP units required in the blended heparin salt is 0.20 times 172, or 34.4 units.

The additional amount of USP potency is preferably supplied by a lithium salt of heparin. A lithium salt of heparin having, for example, 152 USP potency is supplied. The amount of this lithium salt to blend per milligram of the zinc salt of heparin is computed by dividing the 34.4 additional units by the available 152 USP units per milligram potency of this lithium salt. This results in an amount of 0.226 milligrams of the lithium salt to add per one milligram of the zinc salt to obtain the blended heparin salt. The zinc and lithium salts may then be dissolved in a deionized water to uniformly blend the salts together and subsequently dried, such as lyophilized, to produce a powder.

Table 3 below summarizes the blend of the zinc salt of heparin and the lithium salt of heparin of this example that provides $3.63 \times 10^{-4}$ milligrams of zinc per unit of USP potency.

TABLE 3

| Blended Zinc and Lithium Salt of Heparin Anticoagulant | | | |
|---|---|---|---|
| Salt | Milligrams | USP Potency | % Zinc |
| Zinc | 1.0 | 172.0 | 7.5 |
| Lithium | 0.226 | 34.4 | 0.0 |
| Blended | 1.226 | 206.4 | 7.5 |

The blended heparin provides $3.63 \times 10^{-4}$ milligrams of zinc per unit of USP potency, as shown by dividing the 7.5% zinc content by the 206.4 USP potency The blended heparin salt accordingly weighs 1.226 milligrams and provides 206.4 units of activity (USP potency). The blended heparin salt comprises a proportional blend of the zinc salt of heparin of 172 USP potency at 7.5% concentration and the lithium salt of heparin at 152 USP potency.

The blended heparin salt is used by placing a predetermined amount in a sampling syringe. The amount is proportional based on the number of USP units to supply with the syringe and the total USP potency (units) available in the blended heparin salt. For example, a sampling syringe is to have 50 USP units. Dividing the 50 units by the 206.4 total number of USP units available yields a fraction, of about 0.24. The total weight of the blended heparin salt 1.226 milligrams is multiplied by this fraction to determine the proportional amount of the salt (0.294 milligrams) to place in the syringe to provide 50 USP units. The blended heparin salt in the sampling syringe substantially eliminates the skew in the measured amount of ionized calcium in the blood sample imparted by the heparin anticoagulant.

The present invention accordingly comprises a heparin salt anticoagulant that delivers a selected predetermined amount of zinc per USP unit of activity, and a method of blending zinc salts of heparin having different zinc concentrations and heparin activity potencies. In that regard, the heparin salt and test results shown above may be expressed in terms of milligrams of zinc per USP unit of potency, as shown by the tables below. Table 4 illustrates the relationship of the zinc salt and the lithium salt blended on a 1:1 ratio depending on the potency of the zinc salt for Lot 2 in Example 2 discussed above. The weight of the lithium salt to blend with 1 milligram of the zinc salt is computed by dividing the target potency of 165 units by the USP potency (173) of the lithium potency. The blended heparin salt has 1.954 milligrams. The total USP potency is the sum of the potencies of the blended salts. The zinc content is the number of milligrams of zinc in the particular salt.

TABLE 4

| Example 2 (1:1) Zinc:Lithium Blended Heparin | | | |
|---|---|---|---|
| | Salts of Heparin | | |
| | Zinc | Lithium | Blended |
| Weight (mg) | 1.0 | 0.954 | 1.954 |
| Potency (USP) | 165 | 165 | 330 |
| Zinc content (mg) | 0.12 | 0.0 | .12 |

Dividing the 0.12 concentration of zinc by the 330 USP units of potency results in a preferred delivery amount of $3.636 \times 10^{-4}$ milligrams of zinc per USP unit of the blended heparin salt. This preferred delivery amount is used to compute blending ratios of zinc salts having different zinc concentrations.

A range of zinc per unit of USP potency can be determined by considering blended heparin salts in ratios of 1:2 zinc salt to lithium salt (Table 5 below) and in a ratio of 2:1 zinc salt to lithium salt (Table 6 below). These examples in Tables 5 and 6 are based on the salts used for Lot 2 in Example 2. The computed blend starts with 1.0 milligrams of lithium salt. To have a 1:2 zinc to lithium ratio based on potency, the 173 USP units was divided by 2 to have 86.5 USP units provided by the zinc salt. Dividing the 86.5 USP units by the zinc salt USP units per milligram yields 0.524 milligrams of the zinc salt to be blended with the lithium salt. The amount of salt in the blend is the 12% concentration times the 0.524 milligrams, or 0.0688 milligrams.

TABLE 5

| (1:2) Zinc:Lithium Blended Heparin | | | |
|---|---|---|---|
| | Salts of Heparin | | |
| | Zinc | Lithium | Blended |
| Weight (mg) | 0.524 | 1.0 | 1.524 |
| Potency (USP) | 86.5 | 173 | 259.5 |
| Zinc content (mg) | 0.0688 | 0.0 | 0.0688 |

Dividing the 0.0688 concentration of zinc by the 259 USP units of potency results in a delivery amount of $2.42 \times 10^{-4}$ milligrams of zinc per USP unit in the blended heparin salt.

In the 2:1 blend reported in Table 6, the 165 USP units for 1.0 milligrams of zinc was divided by 2 to determine that 82.5 USP units were to be provided by the lithium salt. Dividing the 82.5 USP units by the 173 USP units per milligram of lithium salt results in 0.48 milligrams of lithium salt to blend with the zinc salt.

TABLE 6

| (2:1) Zinc:Lithium Blended Heparin | | | |
|---|---|---|---|
| | Salts of Heparin | | |
| | Zinc | Lithium | Blended |
| Weight (mg) | 1.0 | 0.48 | 1.48 |
| Potency (USP) | 165 | 82.5 | 247.5 |
| Zinc content (mg) | 0.12 | 0.0 | 0.12 |

Dividing the 0.12 concentration of zinc by the 247.5 USP units of potency results in a delivery amount of $4.85 \times 10^{-4}$ milligrams of zinc per USP unit in the blended heparin salt.

Another example is shown in Table 7 below. A zinc salt of heparin is provided with a concentration of 6.12% zinc and USP potency of 149 units/milligram. This zinc salt provides $4.107 \times 10^{-4}$ mg zn/USP unit. A lithium salt of heparin is provided with a USP potency of 176 units/milligram. The blended heparin salt is to provide $3.63 \times 10^{-4}$ milligrams of zinc per USP unit. Dividing the available amount of zinc in the zinc salt by the $3.63 \times 10^{-4}$ predetermined amount of zinc and subtracting 1.0 results in an additional 13.14 percent USP potency required in the blended heparin salt. Multiplying this percentage times the 149 USP potency results in an additional 19.56 USP units to be provided by blending in an amount of the lithium salt of heparin.ABdividing the 19.56 units needed by 176 USP potency of the lithium salt results in 0.11 milligrams of the lithium salt to blend with 1 milligram of the zinc salt.

TABLE 7

Zinc:Lithium Blended Heparin
(Less Than Saturated Zinc Salt)

| | Salts of Heparin | | |
|---|---|---|---|
| | Zinc | Lithium | Blended |
| Weight (mg) | 1.0 | 0.11 | 1.11 |
| Potency (USP) | 149.0 | 19.56 | 168.56 |
| Zinc content (mg) | 0.0612 | 0.0 | 0.612 |

Dividing the 0.612 concentration of zinc by the 168.56 USP units of potency confirms a delivery amount of $3.63 \times 10^{-4}$ milligrams of zinc per USP unit in the blended heparin salt.

The principles, preferred embodiments and modes of operation of the present invention have been described in the foregoing specification. The invention is not to be construed as limited to the particular forms disclosed, because these are regarded as illustrative rather than restrictive. Moreover, variations and changes may be made by those skilled in the art without departing from the spirit of the invention as set forth by the following claims.

What is claimed is:

1. A method of blending a zinc salt of heparin and a lithium salt of heparin to form a blended heparin salt anticoagulant having reduced interference to determining the amount of ionized calcium in a blood sample, the anticoagulant for use in a blood sampling syringe, comprising:

supplying a zinc salt of heparin having a predetermined activity unit potency;

supplying a lithium salt of heparin having a predetermined activity unit potency;

determining a basis salt as being the one of the zinc salt of heparin and the lithium salt of heparin having the lower activity unit potency;

determining a fractional value less than one of the activity unit potencies of the salt with the lower activity unit potency relative to the salt having the higher activity unit potency;

blending by weight in a 1-to-the-fractional value ratio the basis salt to the other of the zinc salt and the lithium salt to form a blended heparin anticoagulant, whereby a selected number of units of the blended heparin anticoagulant, being placed in a bloodsampling syringe with blood drawn from a patient for blood gas analysis, substantially eliminates the skew imparted by the heparin anticoagulant in the measured value of ionized calcium in the blood sample.

2. A method of blending a heparin salt for use as an anticoagulant in a blood sample, the blended heparin salt substantially eliminating a skew in a determined amount of ionized calcium imparted by the heparin anticoagulant in the blood sample, comprising:

providing a zinc salt of heparin having a zinc concentration per unit of heparin potency of an amount equal or exceeding a predetermined amount of zinc per unit of heparin potency to be provided by a blended heparin salt for use as an anticoagulant in a blood sample held in a sampling syringe;

determining the additional units of heparin potency needed to dilutingly add to the zinc salt of heparin, for providing the predetermined amount of zinc per unit of heparin potency in the blended heparin salt, based on a quotient less 1.0 of the zinc concentration in the zinc salt of heparin divided by the predetermined amount of zinc per unit of heparin potency in the blended heparin salt times the heparin potency of the zinc salt of heparin;

providing a lithium salt heparin having a predetermined heparin potency;

determining an amount of the lithium salt of heparin that provides an additional amount of heparin potency by dividing said additional units of heparin potency heeded to dilutingly add to the zinc salt of heparin by the predetermined heparin potency of lithium salt of heparin;

blending the amount of the lithium salt of heparin with the zinc salt of heparin in a ratio of the determined additional amount of heparin potency to 1 by weight respectively to form a blended heparin salt that provides the predetermined amount of zinc per unit heparin potency, whereby the blended heparin salt, being placed in a sampling syringe with a blood sample, substantially eliminates the skew in the measured amount of ionized calcium in the blood sample imparted by the heparin anticoagulant.

* * * * *